United States Patent
Bae et al.

(10) Patent No.: US 8,491,477 B2
(45) Date of Patent: Jul. 23, 2013

(54) ULTRASONIC ESTIMATION OF STRAIN INDUCED BY IN VIVO COMPRESSION

(75) Inventors: Unmin Bae, Seattle, WA (US); Yongmin Kim, Lake Forest Park, WA (US); Vijay Shamdasani, Seattle, WA (US)

(73) Assignee: University of Washington, Seattle, WA (US)

( * ) Notice: Subject to any disclaimer, the term of this patent is extended or adjusted under 35 U.S.C. 154(b) by 678 days.

(21) Appl. No.: 12/444,122

(22) PCT Filed: Oct. 2, 2007

(86) PCT No.: PCT/US2007/080201
§ 371 (c)(1),
(2), (4) Date: Nov. 19, 2009

(87) PCT Pub. No.: WO2008/042905
PCT Pub. Date: Apr. 10, 2008

(65) Prior Publication Data
US 2010/0094131 A1    Apr. 15, 2010

Related U.S. Application Data

(60) Provisional application No. 60/827,865, filed on Oct. 2, 2006.

(51) Int. Cl.
*A61B 8/00*    (2006.01)
*G06K 9/00*    (2006.01)

(52) U.S. Cl.
USPC .......................... 600/438; 600/443; 382/128

(58) Field of Classification Search
USPC ........................... 600/437, 438, 443; 382/128
See application file for complete search history.

(56) References Cited

U.S. PATENT DOCUMENTS

| | | | |
|---|---|---|---|
| 6,277,074 B1 * | 8/2001 | Chaturvedi et al. | 600/437 |
| 7,223,241 B2 | 5/2007 | Radulescu | |
| 2004/0015079 A1 | 1/2004 | Berger et al. | |
| 2004/0034304 A1 * | 2/2004 | Sumi | 600/439 |
| 2004/0116813 A1 * | 6/2004 | Selzer et al. | 600/467 |
| 2004/0210136 A1 * | 10/2004 | Varghese et al. | 600/443 |
| 2006/0173320 A1 | 8/2006 | Radulescu | |
| 2007/0055448 A1 | 3/2007 | Mendrick et al. | |
| 2007/0093716 A1 | 4/2007 | Radulescu | |

(Continued)

FOREIGN PATENT DOCUMENTS

| | | |
|---|---|---|
| WO | 2006/026552 A1 | 3/2006 |
| WO | WO2006026552 | 3/2006 |

OTHER PUBLICATIONS

Wilson et al., "Ultrasonic Measurement of Small Displacements and Deformations of Tissue", Ultrasonic Imaging, vol. 4., Iss. 1, Jan. 1982, pp. 71-82.*

(Continued)

*Primary Examiner* — Long V. Le
*Assistant Examiner* — Katherine Fernandez
(74) *Attorney, Agent, or Firm* — Dorsey & Whitney LLP

(57) ABSTRACT

An in vivo source of compression is used to cause a bodily structure of interest to expand and contract. Ultrasound signals are incident and their echoes are processed by a strain processor. Resulting strain images are freed from noise caused by external sources of compression. A tissue stiffness index is calculated to obtain quantitative measure of stiffness.

25 Claims, 10 Drawing Sheets

U.S. PATENT DOCUMENTS

| | | | |
|---|---|---|---|
| 2008/0285819 | A1 | 11/2008 | Konofagou et al. |
| 2010/0063393 | A1 | 3/2010 | Moradi et al. |
| 2010/0094131 | A1 | 4/2010 | Bae et al. |
| 2010/0121178 | A1 | 5/2010 | Krishnan et al. |
| 2010/0292571 | A1 | 11/2010 | Kim et al. |
| 2011/0130660 | A1 | 6/2011 | Cloutier et al. |

OTHER PUBLICATIONS

Bae, et al., "Thyroid Elastography Using Carotid Artery Pulsation: A Feasibility Study", IEEE Ultrasonics Symposium, Vancouver Canada Oct. 2-6, 2006 vol. 1 Issue C, Oct. 2006, 614-617.

Bae, U et al., "Angular Strain Estimation Method for Elastography", IEEE Transactions on Ultrasonics, Ferroelectrics, and Frequency Control. vol. 54 Issue 12, Dec. 2007, 2653-2661.

Bae, U et al., "Ultrasound Thyroid Elastography Using Carotid Artery Pulsation: Preliminary Study", Journal of Ultrasound in Medicine. vol. 26 Issue 6, Jun. 2007, 797-805.

Capelli, et al., "Fine Needle Cytology of Complex Thyroid Nodules", European Journal of Endocrinology. vol. 157 Issue 4, Oct. 2007, 529-532.

Chow, et al., "Papillary Microcarcinoma of the Thyroid—Prognostic Significance of Lymph Node Metastasis and Multifocality", Cancer. vol. 98 Issue 1, Jul. 2003, 31-40.

"International Search Report and the Written Opinion", PCT/US2007/080201.

Cinthio, et al., "Longitudinal Movements and Resulting Shear Strain of the Arterial Wall", American Journal of Physiology: Heart of Circulatory Physiology. vol. 291 Issue 1, Jul. 2006, H394-H402.

Cooper, et al., "Management Guidelines for Patients with Thyroid Nodules and Differentiated Thyroid Cancer", Thyroid. vol. 16 Issue 2, Feb. 2006, 1-33.

Dighe, et al., "Differential Diagnosis of Thyroid Nodules with US Elastography Using Carotid Artery Pulsation", Radiology. vol. 248 Issue 2, Aug. 2008, 662-669.

Frates, et al., "Management of Thyroid Nodules Detected at U.S: Society of Radiologists in Ultrasound Consensus Conference Statement", Radiology. vol. 237 Issue 3, Dec. 2005, 794-800.

Frates, et al., "Prevalence and Distribution of Carcinoma in Patients with Solitary and Multiple Thyroid Nodules on Sonography", The Journal of Clinical Endocrinol and Metabolism. vol. 91 Issue 9, Sep. 2006, 3411-3417.

Gao, et al., "Imaging of the Elastic Properties of Tissue—A Review", Ultrasound in Medicine and Biology. vol. 22 Issue 8, May 1996, 959-977.

Garra, et al., "Elastography of Breast Lesions: Initial Clinical Results", Radiology. vol. 202 Issue 1, Jan. 1997, 79-86.

Gharib, et al., "American Association of Clinical Endocrinologists, Associazione Medici Endocrinologi, and European Thyroid Association Medical Guidelines for Clinical Practice for the Diagnosis and Management of Thyroid Nodules", Endocrine Practice. vol. 16 Suppl 1, May/Jun. 2010, 1-43.

Gharib , "Chapter 6d. Fine-Needle Aspiration Biopsy of the Thyroid Gland", Thyroid Disease Manager. http://www.thyroidmanager.org/Chapter6a/chapter6d.pdf, Feb. 1, 2008.

Gharib, et al., "Fine-Needle Aspiration Biopsy of the Thyroid: An Appraisal", Annals of Internal Medicine. vol. 118 Issue 4, Feb. 1993, 282-289.

Greenleaf, et al., "Selected Methods for Imaging Elastic Properties of Biological Tissues", Annual Review of Biomedical Engineering 5, Aug. 2003, 57-78.

Hay, et al., "Papillary Thyroid Microcarcinoma: A Study of 900 Cases Observed in a 60-Year Period", Surgery. vol. 144 Issue 6, Dec. 2008, 980-988.

Hegedus, , "Clinical Practice. The Thyroid Nodule", New England Journal of Medicine. vol. 351 Issue 17, Oct. 2004, 1764-1771.

Hegedus, et al., "Management of Simple Nodule Goiter: Current Status and Future Perspectives", Endocrine Reviews. vol. 24 Issue 1, Feb. 2003, 102-132.

Lyshchik, et al., "Elastic Moduli of Thyroid Tissues Under Compression", Ultrasonic Imaging. vol. 27 Issue 2, Apr. 2005, 101-110.

Lyshchik, et al., "Thyroid Gland Tumor Diagnosis at US Elastography", Radiology. vol. 237 Issue 1, Oct. 2005, 202-211.

Mazzaferri, , "Long-Term Impact of Initial Surgical and Medical Therapy on Papillary and Follicular Thyroid Cancer", American Journal of Medicine. vol. 97 Issue 5, Nov. 1994, 418-428.

McCartney, , "Decision Analysis of Discordant Thyroid Nodule Biopsy Guideline Criteria", Journal of Clinical Endocrinology and Metabolism. vol. 93 Issue 8, Aug. 2008.

Moon, et al., "Analysis of Elastographic and B-Mode Features at Sonoelastography for Breast Tumor Classification", Ultrasound in Medicine and Biology. vol. 35 Issue 11, Nov. 2009, 1794-1802.

Moon, et al., "Benign and Malignant Thyroid Nodules: US Differentiation—Multicenter Retrospective Study", Radiology. vol. 247 Issue 3, Jun. 2008, 762-770.

Ophir, et al., "Elastography: A Quantitative Method for Imaging the Elasticity of Biological Tissues", Ultrasonic Imaging. vol. 13 Issue 2, Apr. 1991, 111-134.

Ophir, et al., "Elastography: Ultrasonic Estimation and Imaging of the Elastic Properties of Tissues", Proceedings of the Institution of Mechanical Engineers. Part H: Journal of Engineering in Medicine. vol. 213 Issue 3, Mar. 1, 1999, 203-233.

Ortiz, et al., "Effect of Early Referral to an Endocrinologist on Efficiency and Cost of Evaluation and Development of Treatment Plan in Patients with Thyroid Nodules", Journal of Clinical Endocrinology and Metabolism. vol. 83 Issue 11, Nov. 1998, 3803-3807.

Raab, et al., "Effectiveness of Toyota Process Redesign in Reducing Thyroid Gland Fine-Needle Aspiration Error", American Journal of Clinical Pathology. vol. 126 Issue 4, Oct. 2006, 585-592.

Rago, et al., "Elastography: New Developments in ultrasound for Predicting Malignancy in Thyroid Nodules", Journal of Clinical Endocrinology & Metabolism. vol. 92 Issue 8, Aug. 2007, 2917-2922.

Tan, , "Thyroid Incidentalomas: Management Approaches to Nonpalpable Nodules Discovered Incidentally on Thyroid Imaging", Annals of Internal Medicine. vol. 126 Issue 3, Feb. 1997, 226-231.

Tranquart, et al., "Elastosonography of Thyroid Lesions", Journal of Radiology. vol. 89 Issue 1 Pt 1, Jan. 2008, 35-39.

Wartofsky, , "Thyroid Cancer: A Comprehensive Guide to Clinical Management", Humana Press, Totowa, New Jersey Reviewed by J.E. Freitas in Journal of Nuclear Medicine vol. 42 Issue 6, Jun. 2001, 984-985.

Wilson, et al., "Ultrasonic Measurement of Small Displacements and Deformations of Tissue", Ultrasonic Imaging vol. 4 Iss. 1, 1982, 71-82.

Yeung, , "Management of the Solitary Thyroid Nodule", Oncologist. vol. 13 Issue 2, Feb. 2008, 105-112.

* cited by examiner

ULTRASONIC ESTIMATION OF STRAIN INDUCED BY IN VIVO COMPRESSION

CROSS-REFERENCE TO RELATED APPLICATION

This application claims the benefit of Provisional Application No. 60/827,865, filed Oct. 2, 2006, the benefit of which is hereby claimed under 35 U.S.C. §119 and which is incorporated herein by reference.

BACKGROUND

Over the last two decades, non-invasive, ultrasound-based techniques have been developed to extract tissue stiffness information. A main approach in ultrasound elasticity imaging is to estimate tissue strain caused by compression of bodily structures of interest. Stiff tissue has a high elasticity modulus and therefore shows less strain than soft tissue under applied compression force. By estimating tissue strain induced by applied compression, tissue stiffness information can be obtained.

The reason why researchers are interested in tissue stiffness is because they have found that abnormal cells, such as papillary adenocarcinoma, the most common thyroid cancer, is five times stiffer than normal thyroid tissue, and benign thyroid lesions are 1.7 times stiffer than normal fibroid tissue with a certain amount of compression force. Conventionally, finger palpation, which is used to search for abnormally stiff tissues, has been a primary tool for detecting thyroid nodules that may be abnormal.

To investigate ultrasound strain imaging of the thyroid, researchers applied external compression on the neck area and estimated the resulting strain from ultrasound signals. However, it has been reported that the quality of strain images and the resulting diagnostic performance are significantly affected by the pulsation of the carotid artery and out-of-plane motion during external free-hand compression. Without a solution to solve or reduce the problem, the strain images can be of poor quality, and it may not be possible to develop diagnostic machinery based on strain images.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter. A method, system, and computer-readable medium for calculating stiffness is provided.

In accordance with one aspect of this invention, a method form of the invention includes a method executed on a computer for computing stiffness information of bodily structures without the use of an external compression source. The method comprises transmitting and acquiring ultrasound signals echoed from a bodily structure of interest while the bodily structure is compressed and expanded by an in vivo source of compression proximate to the bodily structure. The method further comprises generating strain images by executing a strain calculation on the ultrasound signals echoed from the bodily structure of interest while the bodily structure of interest is compressed and expanded.

In accordance with another aspect of this invention, a system form of the invention includes a computer system for generating strain images. The computer system comprises a piece of software being executed on the computer system for locating an in vivo source of compression near a bodily structure of interest. The computer system further comprises an ultrasound machine that transmits and receives ultrasound signals echoed from the bodily structure of interest. The computer system yet further comprises a strain processor for generating strain images by using the ultrasound signals echoed from the bodily structure of interest while it expands and compresses as caused by the in vivo source of compression.

In accordance with an additional aspect of this invention, the computer-readable medium form of the invention includes a computer-readable medium having instructions stored thereon to implement a method executed on a computer for computing stiffness information of bodily structures without using external compression source. The computer-readable medium comprises transmitting and acquiring ultrasound signals echoed from a bodily structure of interest while the bodily structure is compressed and expanded by an in vivo source of compression proximate to the bodily structure. The computer-readable medium further comprises generating strain images by executing a strain calculation on the ultrasound signals echoed from the bodily structure of interest while the bodily structure of interest is compressed and expanded.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
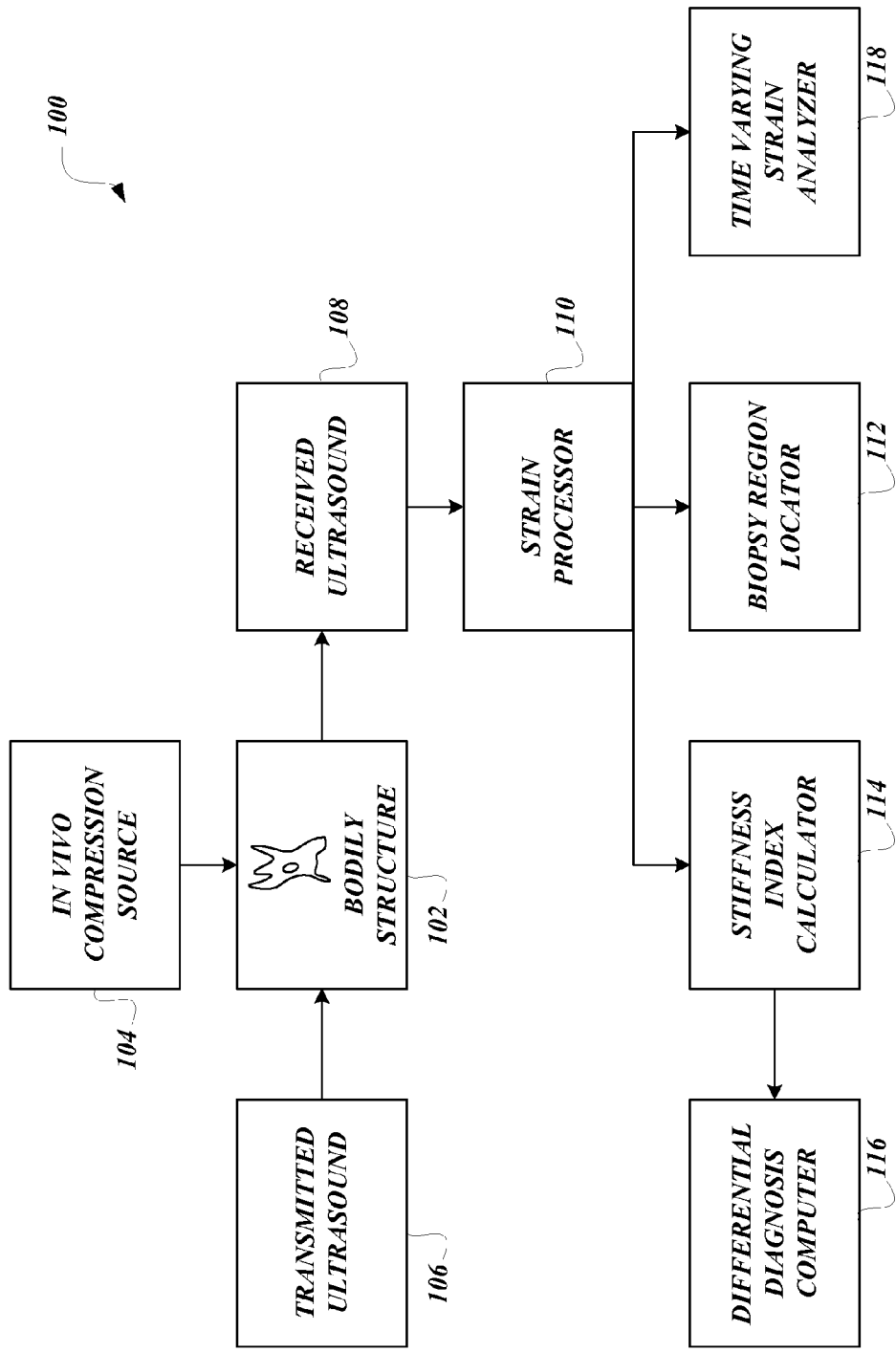
FIG. 1 is a block diagram illustrating an exemplary system for generating strain images of bodily structures of interest without using external compression source.
Figure 2A:
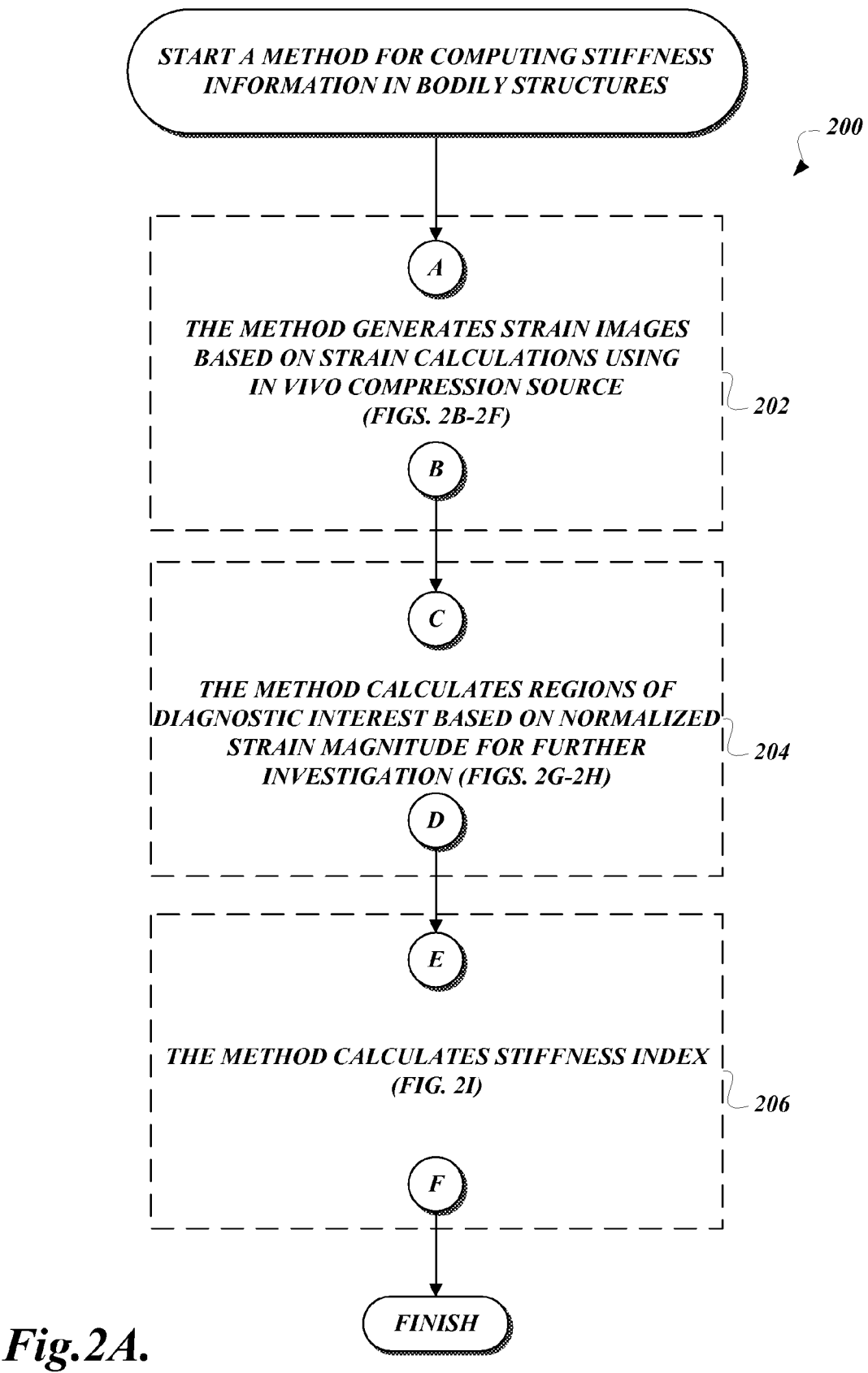
FIGS. 2A-2I are process diagrams illustrating a method for computing stiffness information in bodily structures of interest.
Figure 2B:
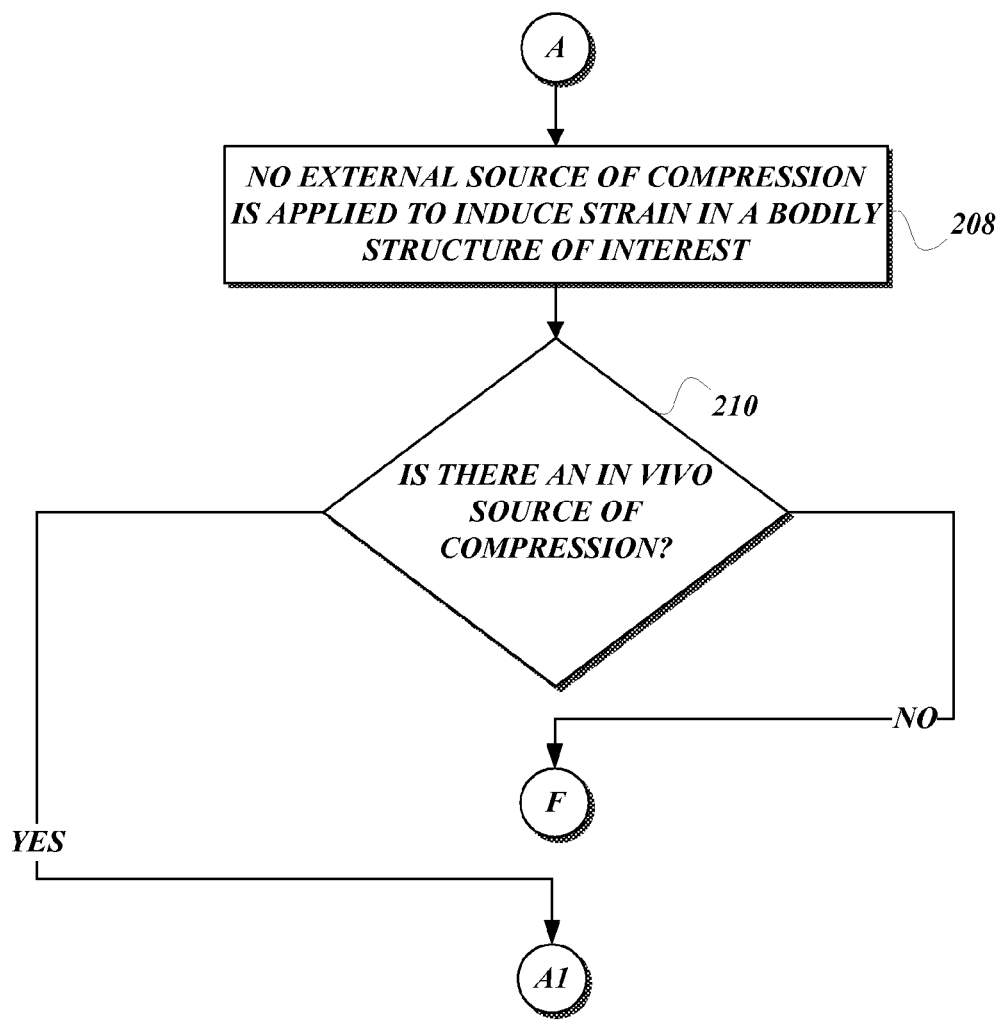
Figure 2C:
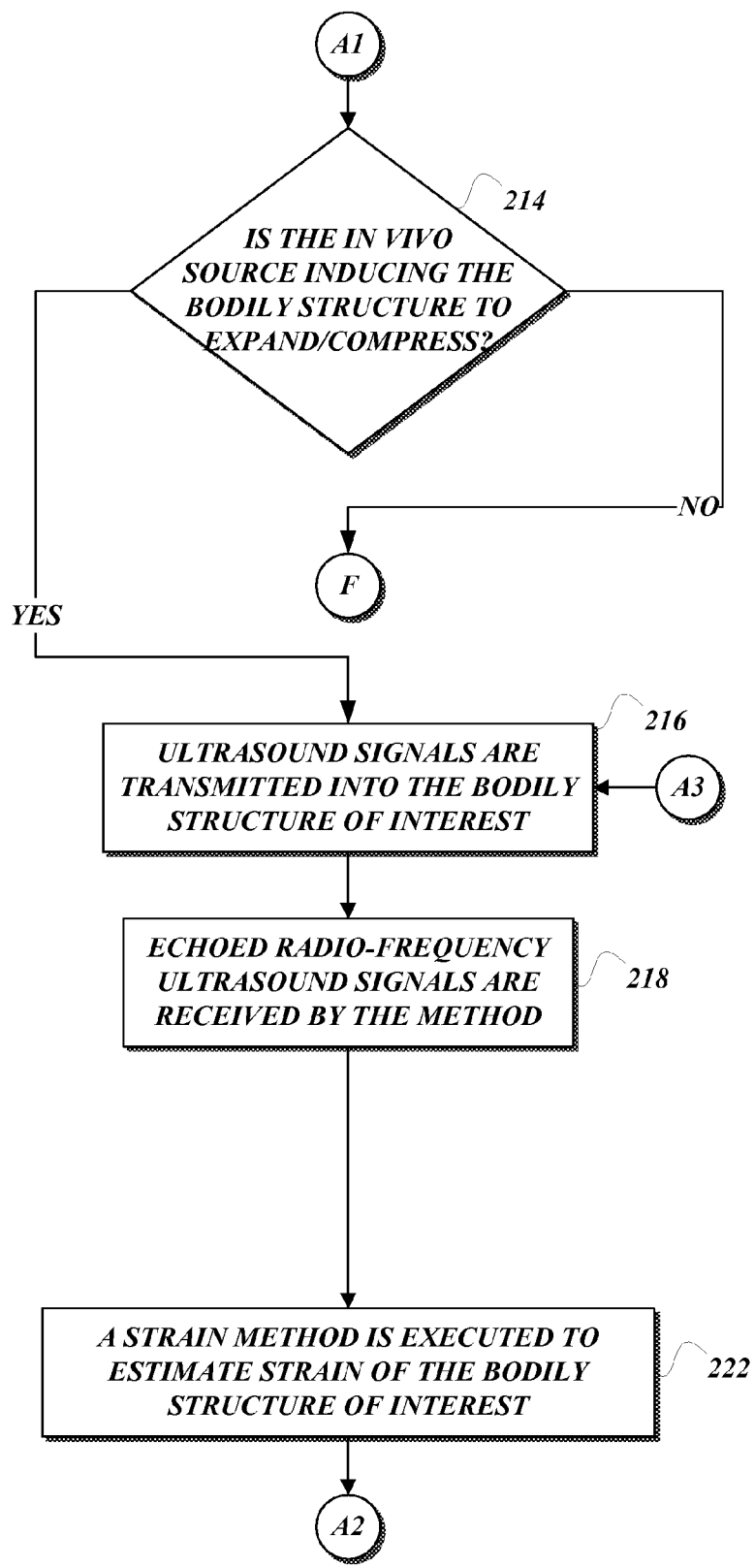
Figure 2D:
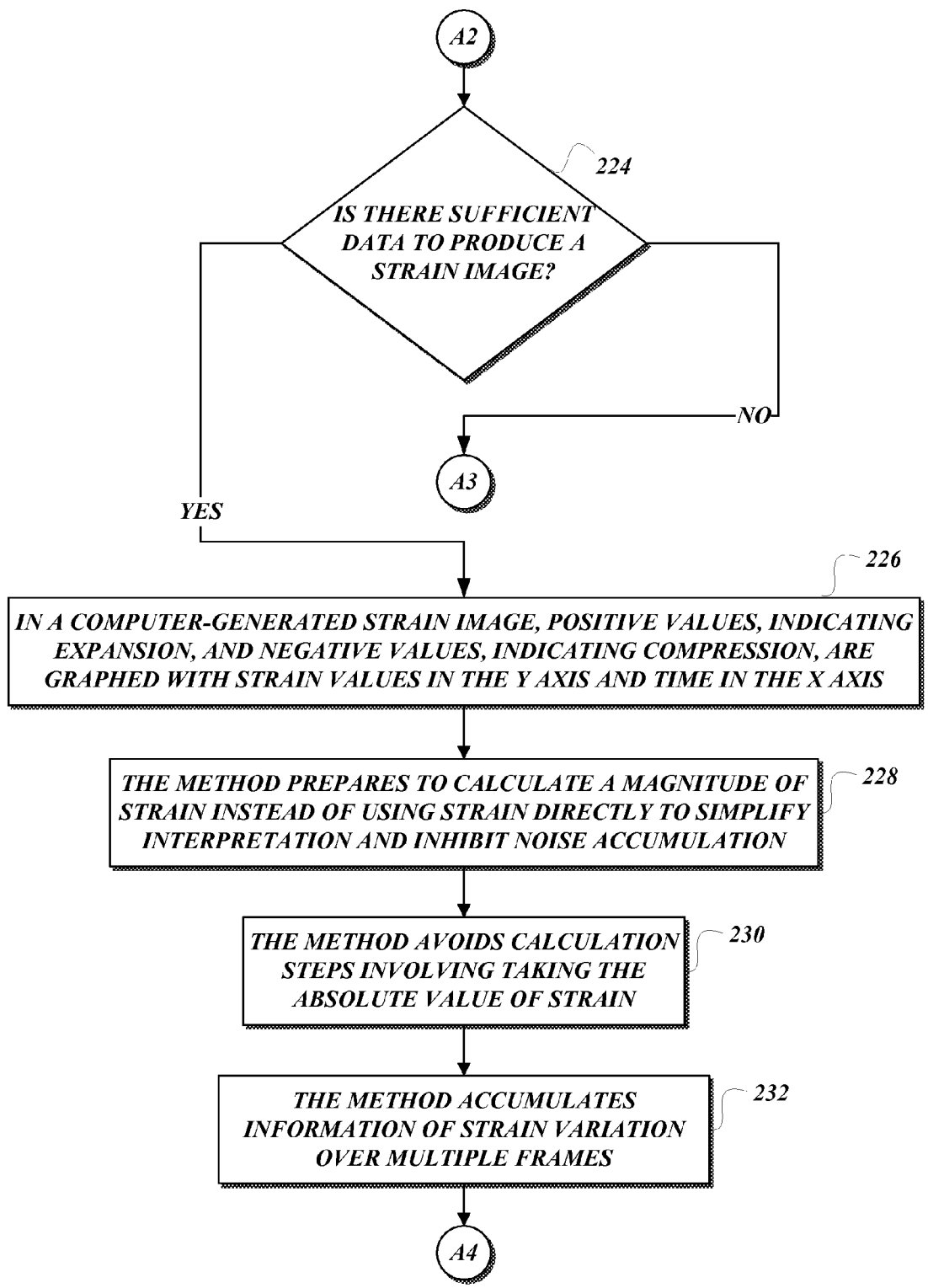
Figure 2E:
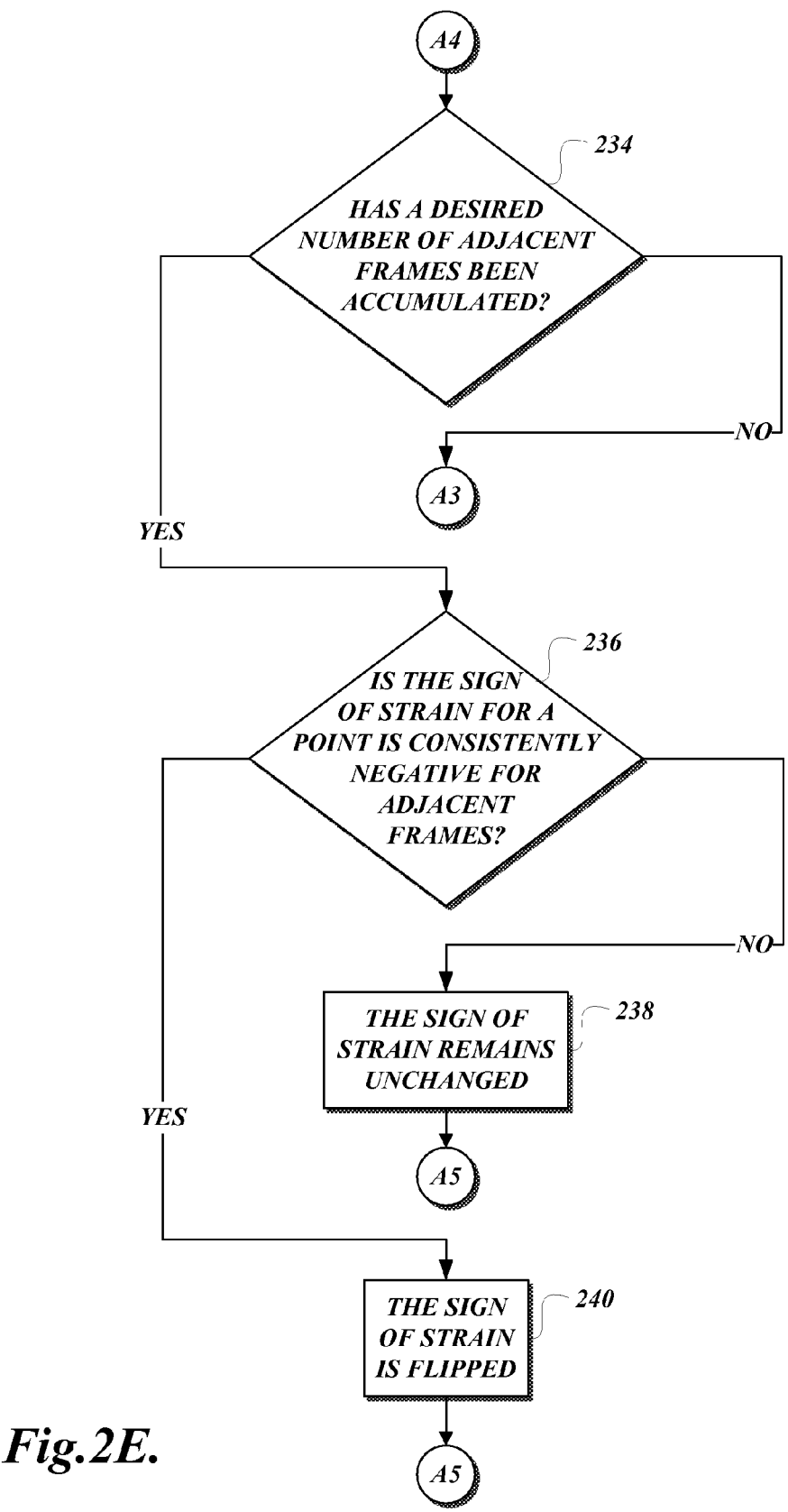
Figure 2F:
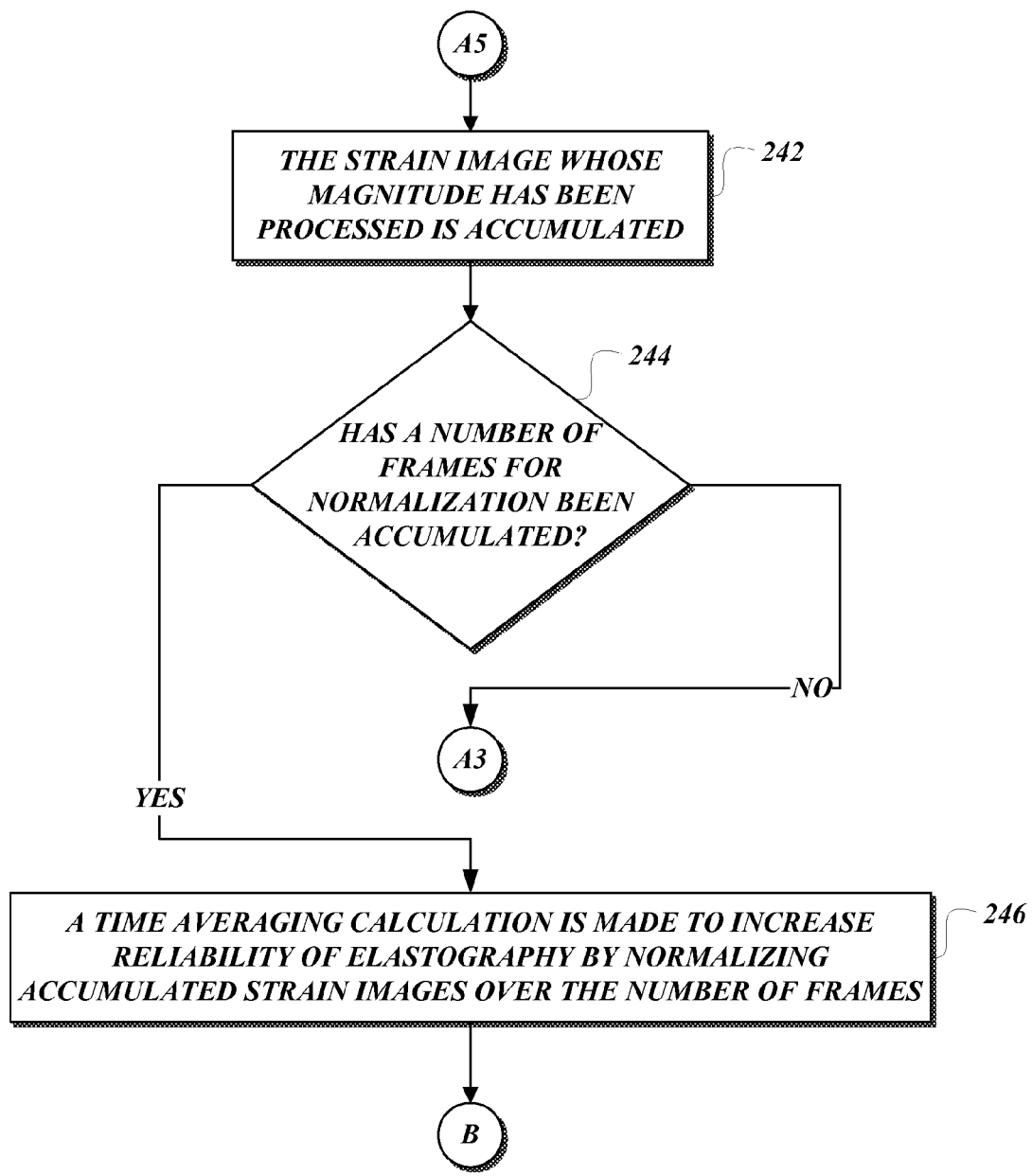
Figure 2G:
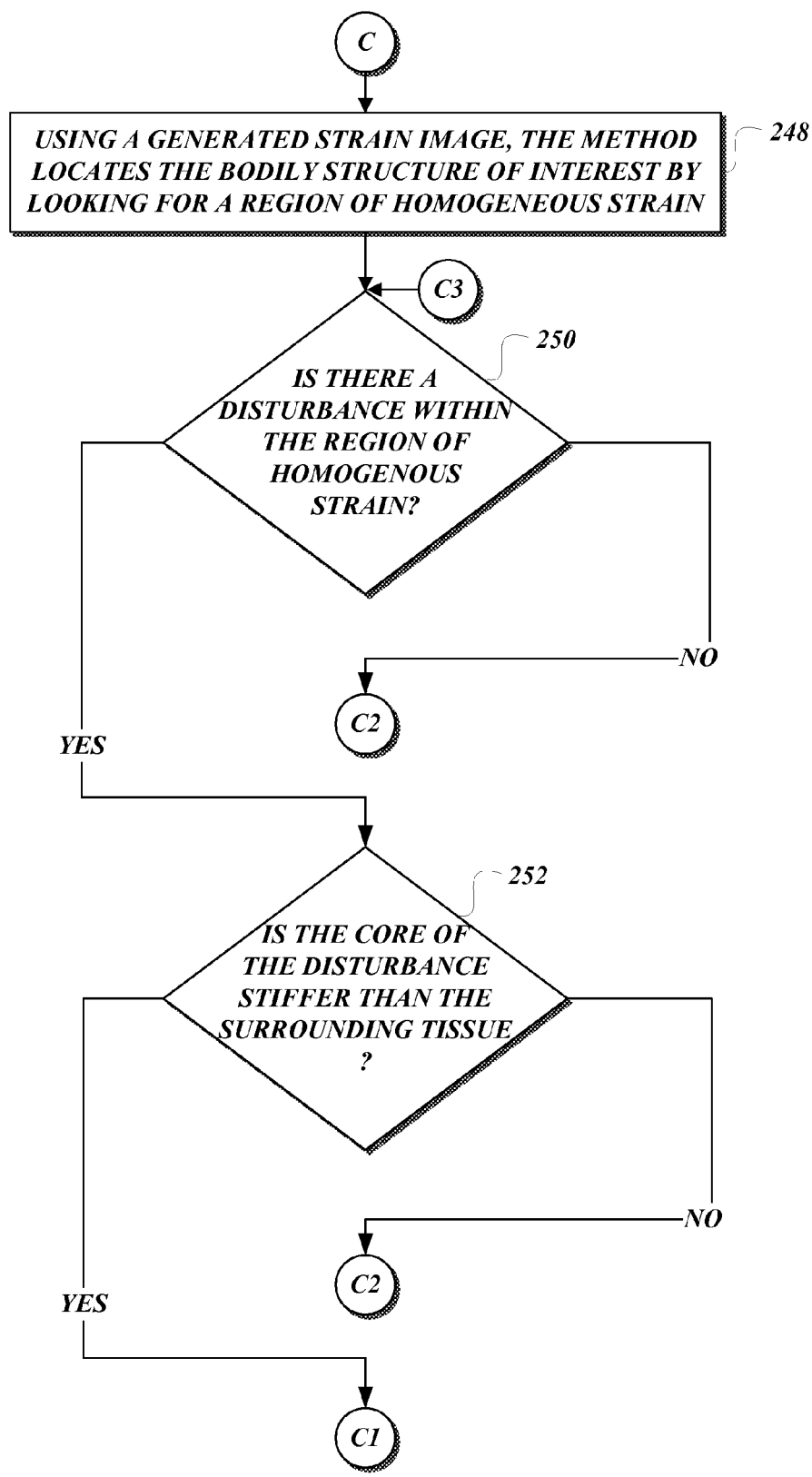
Figure 2H:
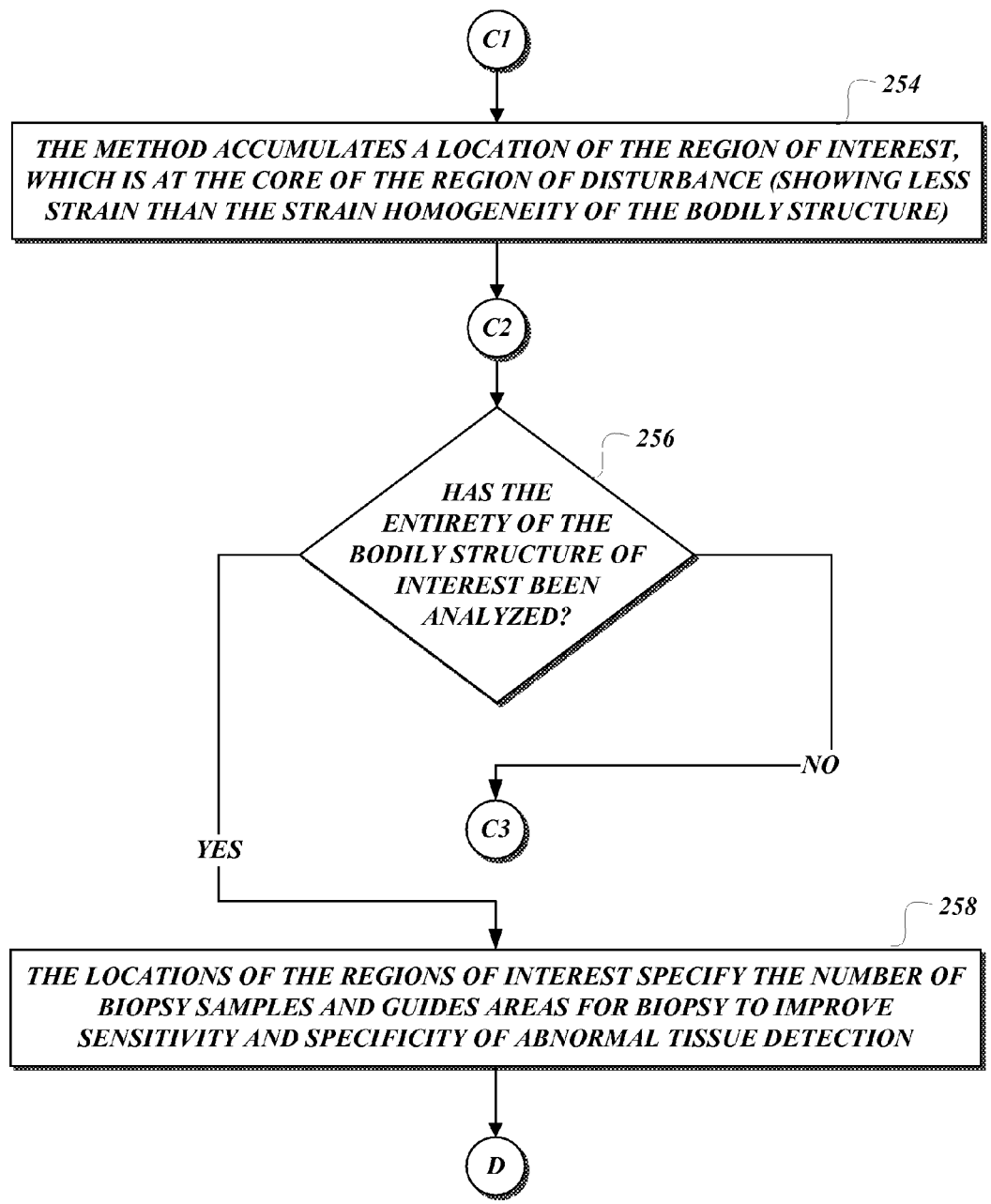
Figure 2I:
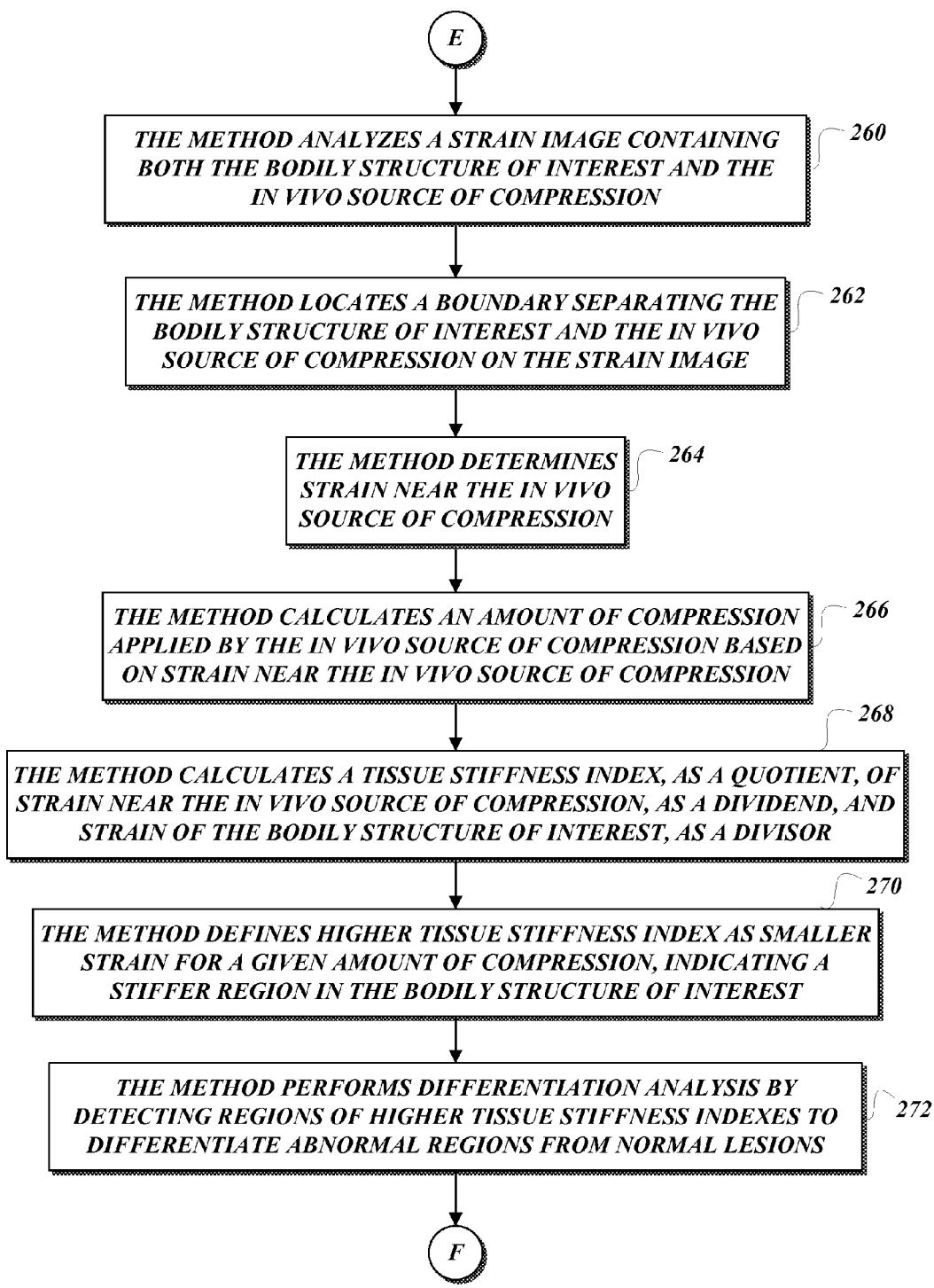

FIG. 1 illustrates a system 100 that generates strain images without using an external compression source. The approach in the system 100 is to enable ultrasound elasticity imaging to estimate tissue strain caused by compression (elastography). Stiff tissue has a high elasticity modulus and shows less strain than softer tissue under similarly applied force. By estimating tissue strain induced by compression, tissue stiffness information can be obtained. The use of in vivo compression source 104 allows the system 100 to reach those internal bodily structures that are not available for the application of external compression sources. Also, even for bodily structures accessible by external compression sources, out-of-plane motion during external compression sources produces poor quality strain images. The system 100 facilitates strain processing techniques to aid interpretation of strain induced by an in vivo compression source.

Initially, a bodily structure 102 of interest is located. The bodily structure includes tissues, aggregates of cells, internal or external organs, and other implanted bodily structures. No external compression source is applied to the bodily structure 102 so as to reduce or eliminate noise caused by out-of-plane motion of free-hand compression force. An in vivo compression source 104 near the bodily structure 102 is located. Such in vivo compression source 104 may include arterial pulsation; pulsation of the carotid artery; pulsation of the abdominal aorta; or wherever the vascular system consisting of arteries and veins provides enough of an in vivo compression force to image the bodily structure 102 for strain calculations. In other words, pulsation of the abdominal aorta could be the compression source for the liver. The in vivo compression source 104 preferably serves as a repeatable and operator-independent compression source for elastography.

Transmitted ultrasound 106 is produced when an ultrasound transducer transmits ultrasound pulses into the bodily structure 102 to be imaged. Received ultrasound 108 represents the ultrasound signals that are reflected back from boundaries of the bodily structure 102, as well as scattering by disturbances in the bodily structure 102 that may be benign lesions or abnormal regions of interest. The bodily structure 102 is compressed or expanded by the in vivo compression source 104 and its deformation is estimated by the system 100 using the received ultrasound 108. For example, where the carotid artery is used as the in vivo compression source 104, during systole, higher blood pressure in the lumen of the carotid artery compresses the arterial wall in the radial direction and compresses a bodily structure of interest against other bodily structures. In case the bodily structure of interest is soft tissue, it is nearly incompressible (i.e., the volume does not change under loading); compression in one direction causes expansion in the other directions. Thus, lateral compression of the bodily structure in systole causes axial expansion of the bodily structure of interest. During diastole, the bodily structure restores to the original state and thus experiences axial compression.

A strain processor 110 calculates strain of the bodily structure 102 as well as the surrounding tissues to create a strain image for subsequent analysis and processing. One example of strain processing is discussed by U.S. patent application Ser. No. 11/574,394, filed on Feb. 27, 2007, titled "Ultrasonic Direct Strain Direct Estimation Using Temporal and Spatial Correlation." Other suitable strain processing can also be used. When a strain image is shown as a graph with strain values in the y-axis and time in the x-axis, the axial expansion of the bodily structure of interest and the compression of the carotid artery wall during systole result in the positive and negative peaks in the strain image. In such a strain image, positive and negative values indicate axial expansion and compression. Both positive and negative values appear in the strain image and the sign of strain changes over an oscillation cycle of the in vivo compression source 104. One with ordinary skill in this art would appreciate that having a negative strain value does not mean the tissue is stiffer than tissue with positive strain. To simplify strain calculations (i.e. smaller strain, stiffer tissue), magnitude of strain may be used instead of strain values when the in vivo compression source 104 is used for elastography.

One or more strain images produced by the angular strain processor 110 are presented to a stiffness index calculator 114. Strain images provide information of the relative stiffness among neighboring tissues; however, strain values within the strain images vary with the amount of applied compression and do not represent the elasticity modulus. Thus, strain values from different patients may not be directly compared to each other for evaluating the difference in tissue stiffness between patients. When the in vivo compression source 104 is used, strain near the in vivo compression source 104 can indicate the amount of compression applied by its oscillation. This information can be utilized to compute a more quantitative measure of tissue stiffness than strain values obtained directly from the strain images. The stiffness index is calculated as a quotient with strain near the in vivo compression source 104 as a dividend and strain of the bodily structure of interest 102 as a divisor.

The stiffness index, if high, means smaller strain for a given amount of compression. The stiffness index can be calculated for all regions inside a bodily structure of interest. Since carcinoma tissue may be stiffer than other tissues, the stiffness index may be used to detect the absence or presence of carcinoma. The information produced by the stiffness index calculator 114 can be presented to a differential diagnosis computer 116 to determine whether the bodily structure 102 contains regions of no interest and/or regions of interest for further carcinoma discovery.

The strain images produced by the angular strain processor 110 can be presented to a biopsy region locator 112. Presently, fine needle aspiration (FNA) biopsy extracts samples from the bodily structure 102 to determine abnormality. Without guidance, the areas of FNA biopsy may return perfectly normal samples and neglect regions of interest within the bodily structure 102 that may be abnormal. The strain images produced by the angular strain processor 110 reveal areas of homogeneity of the bodily structure 102 as well as any disturbances that may show up on the one or more strain image (s). The regions of disturbance may be areas for guiding biopsy to improve sensitivity and specificity in cancer detection and reduce the number of inadequate biopsy extractions with insufficient tissue samples.

The system 100 also includes a time varying strain analyzer 118. In addition to strain contrast provided by one or more strain images produced by the angular strain processor 110, in vivo compression induced strain imaging can be used to monitor variation of strain with respect to time. Strain amplitude may be different between two points in time, but also strain wave form over a cycle of the application of the in vivo compression source 104 may be different. Information of time-variance strain provided by the time varying strain analyzer 118 is not typically available in conventional strain images that show strain at a specific time. Strain time sequences as reviewed by the time-varying strain analyzer 118 may include other tissue mechanical properties, such as visco-elasticity that may be useful in determining the malignancy of bodily structure 102.

FIGS. 2A-2I illustrate a method 200 for computing stiffness information in bodily structures. The method 200 or a portion of it can be implemented by software executing on any programmable computer or by hardware, such as application-specific integrated circuits, field programmable gate arrays, field programmable logic devices, and embedded hardware devices. From a start block, the method 200 proceeds to a set of method steps 202 defined between a continuation terminal ("Terminal A") and another continuation terminal ("Terminal B"). The set of method steps 202 calculates strain images based on strain calculations using in vivo compression source.

From Terminal A (FIG. 2B), the method 200 proceeds to block 208 where no external source of compression is applied to induce strain in a bodily structure of interest, such as the bodily structure 102. The method proceeds to decision block 210 where a test is performed to determine whether an in vivo source of compression exists. If the answer is NO to the test at decision block 210, the method proceeds to another continuation terminal ("Terminal F") and terminates execution. If the answer to the test at decision block 210 is YES, the method continues to another continuation terminal ("Terminal A1").

From Terminal A1 (FIG. 2C), the method 200 proceeds to decision block 214 where a test is performed to determine whether the in vivo source induces the bodily structure to expand and compress. If the answer to the test at decision block 214 is NO, the method 200 proceeds to Terminal F and terminates execution. If the answer to the test at decision block 214 is YES, the method 200 proceeds to block 216 where ultrasound signals are transmitted into the bodily structure of interest. At block 218, echoed ultrasound signals are received by the method. At block 222, a strain method is executed to estimate the strain of the bodily structure of interest. The method 200 then continues to another continuation terminal ("Terminal A2").

From Terminal A2, (FIG. 2D), the method 200 proceeds to decision block 224 where a test is performed to determine whether there is sufficient data to produce a screen image. If the answer to the test at decision block 224 is NO, the method continues to another continuation terminal ("Terminal A3") where the method 200 skips to block 216 (FIG. 2C) and the above-identified processing steps are repeated.

Otherwise, if the answer to the test at decision block 224 is YES, the method 200 continues to block 226 where, in a computer-generated strain image, positive values, indicating expansion, and negative values, indicating compression, are graphed with screen values in the y axis and time in the x axis. The method 200 prepares to calculate a magnitude of strain instead of using strain directly to simplify interpretation and inhibit noise accumulation. See block 228. At block 230, the method avoids calculation steps involving taking the absolute value of strain to obtain the magnitude of strain. At block 232, the method accumulates information of strain variation over multiple adjacent frames. The method 200 then continues to another continuation terminal ("Terminal A4").

From Terminal A4 (FIG. 2E), the method 200 proceeds to decision block 234 where a test is performed to determine whether a desired number of adjacent frames have been accumulated. If the answer to the test at decision block 234 is NO, the method continues to Terminal A3 from where it skips back to block 216 and the above-identified processing steps are repeated. Otherwise, if the answer to the test at decision block 234 is YES, the method continues to another decision block 236 where a test is performed to determine whether the sign of strain for a point is consistently negative for adjacent frames. If the answer to the test at decision block 236 is NO, the sign of strain remains unchanged by the method. See block 238. The method then continues to another continuation terminal ("Terminal A5"). If the answer to the test at decision block 236 is YES, the method continues to block 240 where the sign of strain is flipped. In other words, the method 200 changes the negative polarization of the point to positive polarization. Prior to the time averaging steps discussed below to eliminate or reduce noise, strain magnitude processing needs be executed. To compute the strain magnitude, various embodiments of the present invention avoid simply taking the absolute value of strain to cause conversion of all negative noise values to positive values. The accumulated positive noise values during time averaging steps causing noise amplification instead of noise reduction. To inhibit noise amplification, information of strain variation over frames is used to determine if the sign of strain needs to be changed. This leads to the computing of magnitude of strain for tissues without altering the characteristics of undesired noise. The method 200 then continues to Terminal A5.

From Terminal A5 (FIG. 2F), the method 200 continues to block 242 where the strain image whose magnitude has been processed is accumulated. At decision block 244, a test is performed to determine whether a certain number of frames for normalization has been accumulated. If the answer to the test at decision block 244 is NO, the method continues to Terminal A3 and skips back to block 216 where the above-identified processing steps are repeated. Otherwise, if the answer to the test at decision block 244 is YES, the method continues to block 246 where a time-averaging calculation is made to increase the reliability of elastography by normalizing accumulated strain images over the number of frames. This time averaging can increase the reliability of tissue elastography when the region of interest is set since noise in strain from multiple frames cancel each other out using the time-averaging calculation of various embodiments of the present invention. The method then continues to Terminal B.

From Terminal B (FIG. 2A), the method 200 proceeds to a set of method steps 204 defined between a continuation terminal ("Terminal C") and another continuation terminal ("Terminal D"). The set of method steps 204 calculates regions of diagnostic interest based on normalized strain magnitude for further investigation. From Terminal C (FIG. 2G), using a generated strain image, the method 200 locates the bodily structure of interest by looking for a region of homogeneous strain. See block 248. The method 200 continues to decision block 250 where a test is performed to determine whether there is a disturbance within the region of homogeneous strain. In other words, whether there is a region that appears to have heterogeneous strain. If the answer to the test at decision block 250 is NO, the method continues to another continuation terminal ("Terminal C2"). If the answer to the test at decision block 250 is YES, the method continues to decision block 252 where another test is performed to determine whether the core of the disturbance is stiffer than the surrounding tissue. If the answer to the test at decision block 252 is NO, the method 200 continues to Terminal C2. Otherwise, if the answer to the test at decision block 252 is YES, the method 200 continues to another continuation terminal ("Terminal C1").

From Terminal C1 (FIG. 2H), the method 200 proceeds to block 254 where the method accumulates a location of the region of interest, which is at the core of the regions of disturbance (showing less strain than the strain homogeneity of the bodily structure). The method then continues to Terminal C2 and continues to decision block 256 where another test is performed to determine whether the entirety of the bodily structure of interest has been analyzed. If the answer to the test at decision block 256 is NO, the method continues to another continuation terminal ("Terminal C3") and skips back to decision block 250 (FIG. 2G) where the above-identified processing steps are repeated. Otherwise, if the answer to the test at decision block 256 is YES, the method 200 proceeds to block 258 where the locations of the regions of interest specify the number of biopsy samples and guides areas for a biopsy to be taken to improve sensitivity and specificity of abnormal tissue detection. See block 258. The method then continues to Terminal D.

From Terminal D (FIG. 2A), the method 200 proceeds to a set of method steps 206 defined between a continuation terminal ("Terminal E") and Terminal F. The set of method steps 206 calculates a tissue stiffness index. From Terminal E (FIG. 2I), the method analyzes a strain image containing both the bodily structure of interest and the in vivo source of compression. See block 260. At block 262, the method 200 locates a boundary separating the bodily structure of interest and the in vivo source of compression on the strain image. At block 264, the method 200 determines strain near the in vivo source of compression. The method 200 then calculates an amount of compression applied by the in vivo source of compression based on strain near the in vivo source of compression. See block 266. At block 268, the method 200 calculates a tissue stiffness index, as a quotient, of strain near the in vivo source of compression, as a dividend, and strain of the bodily structure of interest, as a divisor. At block 270, the method 200 defines higher tissue stiffness index as smaller strain for a given amount of compression, indicating a stiffer region in the bodily structure of interest. At block 272, the method performs differentiation analysis by detecting regions of higher tissue stiffness indexes to differentiate abnormal regions from normal regions. The method then continues to Terminal F and terminates execution.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method comprising:
    transmitting and acquiring ultrasound signals echoed from a bodily structure of interest while the bodily structure of interest is compressed and expanded by an oscillating in vivo source of compression proximate to the bodily structure of interest, wherein the bodily structure of interest is compressed and expanded without the application of external compressions to the bodily structure of interest; and
    generating strain images for the bodily structure of interest and the in vivo source of compression by executing a strain calculation on the ultrasound signals echoed from the bodily structure of interest while the bodily structure of interest is compressed and expanded;
    determining a strain of the bodily structure of interest and a strain near the in vivo source of compression from the strain images; and
    computing a quantitative measure of tissue stiffness of the bodily structure of interest by taking a quotient of the strain near the in vivo source of compression and the strain of the bodily structure of interest.

2. The method of claim 1, further comprising terminating the method if the in vivo source of compression does not exist, or if the in vivo source of compression does not induce the bodily structure of interest to expand or compress.

3. The method of claim 1, further comprising generating a strain image, of which positive values indicate expansion of the bodily structure of interest and negative values indicate compression of the bodily structure of interest, in the form of a graph with strain values in the y axis and time in the x axis.

4. The method of claim 1, further comprising calculating the magnitude of strain without taking the absolute value of strain to inhibit accumulation of noise.

5. The method of claim 4, further comprising inhibiting accumulation of noise by flipping the sign of strain if the sign of strain for a point has been consistently negative for a number of adjacent frames and refraining from flipping the sign of strain if the sign of strain for the point has not been consistently negative for the number of adjacent frames.

6. The method of claim 5, further comprising time averaging by taking a quotient of accumulated strain images as the dividend and number of frames as the divisor so as to reduce noise.

7. The method of claim 1, further comprising locating regions of diagnostic interest by determining the bodily structure of interest on a strain image, which appears as an area of homogeneous strain, and finding disturbances within the area of homogeneous strain by looking for heterogeneous strain regions.

8. The method of claim 7, further comprising equating the number of disturbances as the number of biopsy samples to be taken and the locations of the biopsy samples on the bodily structure of interest to be the locations of the disturbances.

9. The method of claim 1, wherein the quantitative measure of tissue stiffness comprises a tissue stiffness index and wherein said taking a quotient includes utilizing the strain near the in vivo source of compression as a dividend, and utilizing the strain of the bodily structure of interest as a divisor.

10. The method of claim 1, wherein computing a quantitative measure of tissue stiffness comprises calculating an amount of compression based on the strain near the in vivo source of compression.

11. A system for generating strain images, the system comprising:
    an ultrasound machine configured to transmit and receive ultrasound signals echoed from a bodily structure of interest during expansion and compression of the bodily structure of interest responsive to an in vivo source of compression near the bodily structure of interest without the application of external compressions to the bodily structure of interest;
    a strain processor for generating strain images for the bodily structure of interest and the in vivo source of compression by using the ultrasounds signals echoed from the bodily structure of interest; and
    a stiffness index calculator configured to determine a strain of the bodily structure of interest and a strain near the in vivo source of compression from the strain images and compute a quantitative measure of tissue stiffness of the bodily structure of interest by taking a quotient of the strain proximate to the in vivo source of compression and the strain of the bodily structure of interest.

12. The system of claim 11, wherein the quotient includes strain proximate to the in vivo source of compression as a dividend, and strain of the bodily structure of interest as a divisor.

13. The system of claim 11, further comprising a biopsy region locator configured to locate regions of disturbances within a homogeneity strain of the bodily structure of interest, the number of regions being the number of biopsy samples and the regions being locations for biopsy samples to be taken.

14. The system of claim 11, further comprising a time varying strain analyzer configured to monitor variation of strain with respect to time.

15. The system of claim 11, wherein computing a quantitative measure of tissue stiffness comprises calculating an amount of compression based on the strain near the in vivo source of compression.

16. A non-transitory computer-readable medium having instructions stored thereon that, when executed, cause a computing system to perform operations comprising:
    receiving ultrasound signals echoed from a bodily structure of interest while the bodily structure of interest is compressed and expanded by an in vivo source of compression proximate to the bodily structure of interest, wherein the bodily structure of interest is compressed and expanded without the application of external compressions to the bodily structure of interest;
    generating strain images for the bodily structure of interest and the in vivo source of compression by executing an angular strain calculation on the ultrasound signals echoed from the bodily structure of interest while the bodily structure of interest is compressed and expanded;
    determining a strain of the bodily structure of interest and a strain near the in vivo source of compression from the strain images; and
    computing a quantitative measure of tissue stiffness of the bodily structure of interest by taking a quotient of the strain near the in vivo source of compression and the strain of the bodily structure of interest.

17. The computer-readable medium of claim 16, wherein the operations further comprise terminating the operations if the oscillating in vivo source of compression does not exist, or if the in vivo source of compression does not induce the bodily structure of interest to expand or compress.

18. The computer-readable medium of claim 16, wherein the operations further comprise generating a strain image, of which positive values indicate expansion of the bodily structure of interest and negative values indicate compression of the bodily structure of interest, in a form of a graph with strain values in the y axis and time in the x axis.

19. The computer-readable medium of claim 16, wherein the operations further comprise calculating the magnitude of strain without taking the absolute value of strain so as to inhibit accumulation of noise.

20. The computer-readable medium of claim 19, wherein the operations further comprise inhibiting accumulation of noise by flipping the sign of strain if the sign of strain for a point has been consistently negative for a number of adjacent frames and refraining from flipping the sign of strain if the sign of strain for the point has not been consistently negative for a number of adjacent frames.

21. The computer-readable medium of claim 20, wherein the operations further comprise time averaging by taking a quotient of accumulated strain images as a dividend and the number of frames as a divisor so as to reduce noise.

22. The computer-readable medium of claim 16, wherein the operations further comprise locating regions of diagnostic interest by determining the bodily structure of interest on a strain image, which appears as an area of homogeneous strain, and finding disturbances within the area of homogeneous strain by looking for heterogeneous strain regions.

23. The computer-readable medium of claim 22, wherein the operations further comprise equating the number of disturbances as the number of biopsy samples to be taken and the locations of the biopsy samples on the bodily structure of interest be the locations of the disturbances.

24. The computer-readable medium of claim 16, wherein the quantitative measure of tissue stiffness comprises a tissue stiffness index and wherein the taking a quotient includes using strain near the in vivo source of compression as a dividend, and using strain of the bodily structure of interest as a divisor.

25. The computer-readable medium of claim 16, wherein computing a quantitative measure of tissue stiffness comprises calculating an amount of compression based on the strain near the in vivo source of compression.

* * * * *